United States Patent
Burg et al.

(10) Patent No.: US 6,340,742 B1
(45) Date of Patent: Jan. 22, 2002

(54) ERYTHROPOIETIN CONJUGATES

(75) Inventors: Josef Burg, Weilheim; Bernd Hilger, Penzberg; Hans-Peter Josel, Weilheim, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/604,871

(22) Filed: Jun. 28, 2000

Related U.S. Application Data

(60) Provisional application No. 60/142,243, filed on Jul. 2, 1999, provisional application No. 60/147,452, filed on Aug. 5, 1999, and provisional application No. 60/151,454, filed on Aug. 30, 1999.

(51) Int. Cl.[7] .................... A61K 38/18; C07K 14/505
(52) U.S. Cl. .................... 530/351; 424/85.1; 530/408
(58) Field of Search .................... 424/85.1; 514/2, 514/8, 12, 21; 530/351, 404, 408

(56) References Cited

U.S. PATENT DOCUMENTS

| | | | |
|---|---|---|---|
| 5,359,030 A | 10/1994 | Ekwuribe | 530/303 |
| 5,547,933 A | 8/1996 | Lin | 514/8 |
| 5,643,575 A | 7/1997 | Martinez et al. | 424/194.1 |
| 5,674,534 A | 10/1997 | Zale et al. | 424/501 |
| 5,759,818 A | * 6/1998 | Boime | 435/69.7 |
| 5,919,455 A | 7/1999 | Greenwald et al. | 424/178.1 |
| 5,919,758 A | * 7/1999 | Sytkowski | 514/8 |
| 5,932,462 A | 8/1999 | Harris et al. | 435/188 |
| 6,025,324 A | 2/2000 | Bailon et al. | 514/2 |
| 6,025,325 A | 2/2000 | Campfield et al. | 514/2 |

FOREIGN PATENT DOCUMENTS

| | | |
|---|---|---|
| DE | 3924705 | 1/1991 |
| EP | 267 678 | 5/1988 |
| EP | 343 635 | 11/1989 |
| EP | 481 791 | 4/1992 |
| EP | 510 356 | 10/1992 |
| EP | 593 868 | 4/1994 |
| EP | 605 963 | 7/1994 |
| EP | 640 619 | 3/1995 |
| WO | WO 86/04068 | 7/1986 |
| WO | WO 88/00967 | 2/1988 |
| WO | WO 94/28024 | 12/1994 |
| WO | WO 95/11924 | 5/1995 |
| WO | WO 95/13090 | 5/1995 |
| WO | WO 95/21629 | 8/1995 |
| WO | WO 96/35718 | 11/1996 |

OTHER PUBLICATIONS

Egrie, J.C. et al., Immunobiol. 172:213–224 (1986).
Monfardini et al., Bioconjugate Chemistry 6, p. 62–69 (1995).
Morpurgo, M. et al., J. Bioconj. Chem. 7, p. 363 (1996).
Abstract for B1, DE 3,924,705 (Jan. 31, 1991).

\* cited by examiner

*Primary Examiner*—Jeffrey E. Russel
(74) *Attorney, Agent, or Firm*—George W. Johnston; Dennis P. Tramaloni; F. Aaron Dubberley

(57) ABSTRACT

Erythropoietin glycoprotein products are disclosed which have the in vivo biological activity of causing bone marrow cells to increase production of reticulocytes and red blood cells. The present conjugates have an increased circulating half-life and plasma residence time, decreased clearance, and increased clinical activity in vivo. In addition, compared with conventional PEG-EPO conjugates, the conjugates of this invention have superior clinical properties. The present invention also includes a method for the treatment of anemia in a human employing the novel erythropoietin glycoprotein products as well as a method for preparing the erythropoietin glycoprotein products.

89 Claims, 3 Drawing Sheets

FIGURE 1

Ala Pro Pro Arg Leu Ile Cys Asp Ser Arg$^{10}$ Val Leu Glu Arg Tyr Leu Leu Glu Ala Lys$^{20}$

Glu Ala Glu Asn Ile Thr Thr Gly Cys Ala$^{30}$ Glu His Cys Ser Leu Asn Glu Asn Ile Thr$^{40}$

Val Pro Asp Thr Lys Val Asn Phe Tyr Ala$^{50}$ Trp Lys Arg Met Glu Val Gly Gln Gln Ala$^{60}$

Val Glu Val Trp Gln Gly Leu Ala Leu Leu$^{70}$ Ser Glu Ala Val Leu Arg Gly Gln Ala Leu$^{80}$

Leu Val Asn Ser Ser Gln Pro Trp Glu Pro$^{90}$ Leu Gln Leu His Val Asp Lys Ala Val Ser$^{100}$

Gly Leu Arg Ser Leu Thr Thr Leu Leu Arg$^{110}$ Ala Leu Gly Ala Gln Lys Glu Ala Ile Ser$^{120}$

Pro Pro Asp Ala Ala Ser Ala Ala Pro Leu$^{130}$ Arg Thr Ile Thr Ala Asp Thr Phe Arg Lys$^{140}$

Leu Phe Arg Val Tyr Ser Asn Phe Leu Arg $^{150}$Gly Lys Leu Lys Leu Tyr Thr Gly Glu Ala$^{160}$

Cys Arg Thr Gly Asp$^{165}$

FIGURE 2

Ala Pro Pro Arg Leu Ile Cys Asp Ser Arg$^{10}$ Val Leu Glu Arg Tyr Leu Leu Glu Ala Lys$^{20}$

Glu Ala Glu Asn Ile Thr Thr Gly Cys Ala$^{30}$ Glu His Cys Ser Leu Asn Glu Asn Ile Thr$^{40}$

Val Pro Asp Thr Lys Val Asn Phe Tyr Ala$^{50}$ Trp Lys Arg Met Glu Val Gly Gln Gln Ala$^{60}$

Val Glu Val Trp Gln Gly Leu Ala Leu Leu$^{70}$ Ser Glu Ala Val Leu Arg Gly Gln Ala Leu$^{80}$

Leu Val Asn Ser Ser Gln Pro Trp Glu Pro$^{90}$ Leu Gln Leu His Val Asp Lys Ala Val Ser$^{100}$

Gly Leu Arg Ser Leu Thr Thr Leu Leu Arg$^{110}$ Ala Leu Gly Ala Gln Lys Glu Ala Ile Ser$^{120}$

Pro Pro Asp Ala Ala Ser Ala Ala Pro Leu$^{130}$ Arg Thr Ile Thr Ala Asp Thr Phe Arg Lys$^{140}$

Leu Phe Arg Val Tyr Ser Asn Phe Leu Arg $^{150}$Gly Lys Leu Lys Leu Tyr Thr Gly Glu Ala$^{160}$

Cys Arg Thr Gly Asp Arg$^{166}$

SEQUENCE LISTING

```
<160> NUMBER OF SEQ ID NOS: 3

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
 1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
 1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80
```

```
Leu Val Asn Ser Ser Gln Pro Trp Glu Pro Leu Gln Leu His Val Asp
            85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 3
<211> LENGTH: 28
<212> TYPE: PRT
<213> ORGANISM: Homo sapiens

<400> SEQUENCE: 3

Ser Ser Ser Ser Lys Ala Pro Pro Pro Ser Leu Pro Ser Pro Ser Arg
  1             5                  10                  15

Leu Pro Gly Pro Ser Asp Thr Pro Ile Leu Pro Gln
            20                  25
```

ERYTHROPOIETIN CONJUGATES

This application claims priority under 35 U.S.C. §119(e) of provisional application(s) Ser. No. 60/142,243, filed Jul. 2, 1999, Ser. No. 60/147,452, filed Aug. 5, 1999 and Ser. No. 60/151,454, filed Aug. 30, 1999.

BACKGROUND OF THE INVENTION

Erythropoiesis is the production of red blood cells which occurs to offset cell destruction. Erythropoiesis is a controlled physiological mechanism that enables sufficient red blood cells to be available for proper tissue oxygenation. Naturally occurring human erythropoietin (hEPO) is a glycoprotein containing 165 amino acids that is produced in the kidney and is the humoral plasma factor which stimulates red blood cell production (Carnot, P and Deflandre, C (1906) C.R. Acad. Sci. 143: 432; Erslev, A J (1953 Blood 8: 349; Reissmann, K R (1950) Blood 5: 372; Jacobson, L O, Goldwasser, E, Freid, W and Plzak, L F (1957) Nature 179: 6331–4). Human EPO stimulates the division and differentiation of committed erythroid progenitors in the bone marrow. Human EPO exerts its biological activity by binding to receptors on erythroid precursors (Krantz, B S (1991) Blood 77: 419). Naturally occurring human erythropoietin is an acidic glycoprotein present in low concentrations in plasma to stimulate replacement of red blood cells which are lost through aging.

Erythropoietin has been manufactured biosynthetically using recombinant DNA technology (Egrie, J C, Strickland, T W, Lane, J et al. (1986) Immunobiol. 72: 213–224) and is the product of a cloned human EPO gene inserted into and expressed in the ovarian tissue cells of the chinese hamster (CHO cells). Naturally occurring human EPO is first translated to a 166 aa containing polypeptide chain with arginine 166. In a postranslational modification arginine 166 is cleaved by a carboxypeptidase. The primary structure of human EPO (165 aa) is illustrated in FIG. 1 (SEQ ID NO:1). The primary structure of human EPO (166 aa) is illustrated in FIG. 2 (SEQ ID NO:2). There are two disulfide bridges between $Cys^7$-$Cys^{161}$ and $Cys^{29}$-$Cys^{33}$. The molecular weight of the polypeptide chain of human EPO without the sugar moieties is 18,236 Da. In the intact EPO molecule, approximately 40% of the molecular weight is accounted for by the carbohydrate groups (Sasaki, H, Bothner, B, Dell, A and Fukuda, M (1987) J. Biol. Chem. 262: 12059).

Because erythropoietin is essential in red blood cell formation, the hormone is useful in the treatment of blood disorders characterized by low or defective red blood cell production. Clinically, EPO is used in the treatment of for example anemia in chronic renal failure patients (CRF) (Eschbach, J W, Egri, J C, Downing, M R et al. (1987) NEJM 316: 73–78; Eschbach, J W, Abdulhadi, M H, Browne, J K et al. (1989) Ann. Intern. Med. 111: 992; Egrie, J C, Eschbach, J W, McGuire, T, Adamson, J W (1988) Kidney Intl. 33: 262; Lim, V S, Degowin, R L, Zavala, D et al. (1989) Ann. Intern. Med. 110: 108–114) and in AIDS and cancer patients undergoing chemotherapy (Danna, R P, Rudnick, S A, Abels, R I In: M B, Garnick, ed. Erythropoietin in Clinical Applications—An International Perspective. New York, N.Y.: Marcel Dekker;1990: p. 301–324). However, the bioavailability of currently available protein therapeutics such as EPO is limited by their short plasma half-life and susceptibility to protease degradation. These shortcomings prevent them from attaining maximum clinical potency.

SUMMARY OF THE INVENTION

Accordingly, the present invention is a new class of PEG derivatives of EPO. The physiologically active PEG-EPO conjugates of this invention comprise an erythropoietin glycoprotein having at least one free amino group and having the in vivo biological activity of causing bone marrow cells to increase production of reticulocytes and red blood cells and selected from the group consisting of human erythropoietin and analogs thereof which have the primary structure of human erythropoietin modified by the addition of from 1 to 6 glycosylation sites; said glycoprotein being covalently linked to from one to three lower-alkoxy poly (ethylene glycol) groups, each poly(ethylene glycol) group being covalently linked to the glycoprotein via a linker of the formula —C(O)—X—S—Y— with the C(O) of the linker forming an amide bond with one of said amino groups, X is —$(CH_2)_k$— or —$CH_2(O$—$CH_2$—$CH_2)_k$—, k is from 1 to 10, Y is

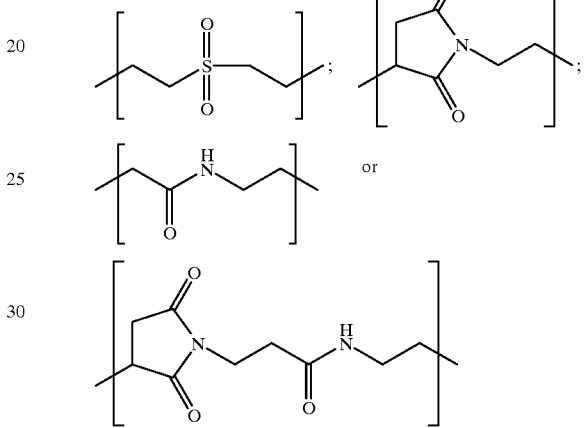

the average molecular weight of each poly(ethylene glycol) moiety is from about 20 kilodaltons to about 40 kilodaltons, and the molecular weight of the conjugate is from about 51 kilodaltons to about 175 kilodaltons.

Compared to unmodified EPO (i.e., EPO without a PEG attached) and conventional PEG-EPO conjugates, the present conjugates have an increased circulating half-life and plasma residence time, decreased clearance, and increased clinical activity in vivo. The conjugates of this invention have the same uses as EPO. In particular, the conjugates of this invention are useful to treat patients by stimulating the division and differentiation of committed erythroid progenitors in the bone marrow in the same way EPO is used to treat patients.

The present invention also includes a method for the treatment of anemia in a human. The present invention also includes a method for preparing the erythropoietin glycoprotein products which comprises covalently reacting an ε-amino group of a lysine amino acid of an erythropoietin protein with a bi-functional reagent to form an intermediate with an amide linkage. The bi-functional reagent contains a reactive group and a protected thiol group. The amide-linked intermediate is then covalently reacted with an activated polyethylene glycol derivative to form the erythropoietin glycoprotein product of the present invention.

DESCRIPTION OF THE DRAWINGS

FIG. 1: Primary structure of human EPO (165 amino acids) (SEQ ID NO:1).

FIG. 2: Primary structure of human EPO (166 amino acids) (SEQ ID NO:2)

DETAILED DESCRIPTION OF THE INVENTION

Definitions

Figure 3:
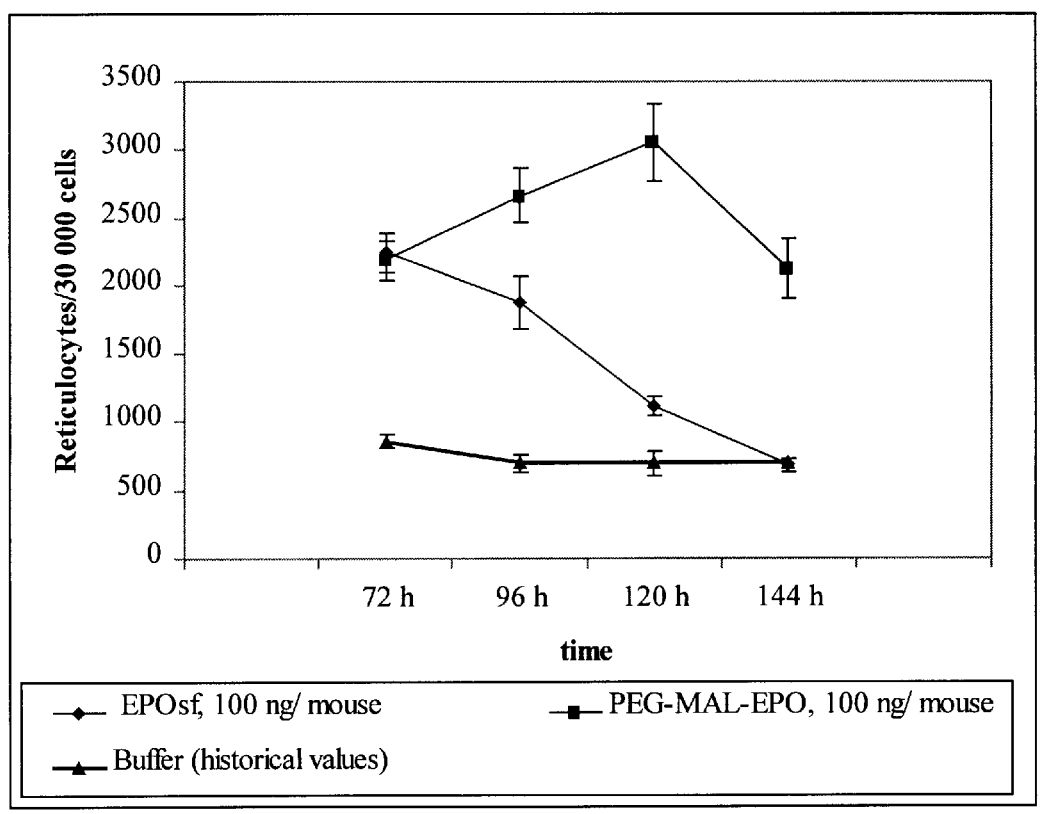
FIG. 3: In vivo activity of pegylated EPO determined by normocythaemic mouse assay.

The following terms shall have the definitions set out below:

The term "erythropoietin protein", "erythropoietin", "EPO", or "erythropoietin glycoprotein" refers to a glycoprotein having the sequence shown in FIG. 1 (SEQ ID NO:1) or FIG. 2 (SEQ ID NO:2), or a protein or polypeptide substantially homologous thereto, whose biological properties relate to the stimulation of red blood cell production and the stimulation of the division and differentiation of committed erythroid progenitors in the bone marrow. As used herein the term EPO protein includes such proteins modified deliberately, as for example, by site directed mutagenesis or accidentally through mutations. These terms also include analogs having from 1 to 6 additional glyosylation sites, analogs having at least one additional amino acid at the carboxy terminal end of the protein wherein the additional amino acid(s) includes at least one glycosylation site, and analogs having an amino acid sequence which includes a rearrangement of at least one glycosylation site, such as for example the analogs disclosed in European Patent Publication No. 640 619. These terms include both natural and recombinantly produced human erythropoietin.

The term "substantially homologous" means that a particular subject sequence, for example, a mutant sequence, varies from a reference sequence by one or more substitutions, deletions, or additions, the net effect of which does not result in an adverse functional dissimilarity between the reference and subject sequences. For purposes of the present invention, sequences having greater than 95 percent homology, equivalent biological properties, and equivalent expression characteristics are considered substantially homologous. For purposes of determining homology, truncation of the mature sequence should be disregarded. Sequences having lesser degrees of homology, comparable bioactivity, and equivalent expression characteristics are considered substantial equivalents.

The term "fragment" of the EPO protein means any protein or polypeptide having the amino acid sequence of a portion or fragment of an EPO protein, and which has the biological activity of the EPO. Fragments include proteins or polypeptides produced by proteolytic degradation of the EPO protein or produced by chemical synthesis by methods routine in the art. An EPO protein or fragment thereof is biologically active when administration of the protein or fragment to man results in the stimulation of red blood cell production and the stimulation of the division and differentiation of committed erythroid progenitors in the bone marrow. Determining such biological activity of the EPO protein can carried out by conventional, well known tests utilized for such purposes on one or more species of mammals. An appropriate test which can be utilized to demonstrate such biological activity is described herein. The term "therapeutically effective amount" is that amount of erythropoietin glycoprotein product necessary for the in vivo biological activity of causing bone marrow cells to increase production of reticulocytes and red blood cells. The exact amount of erythropoietin glycoprotein product is a matter of preference subject to such factors as the exact type of condition being treated, the condition of the patient being treated, as well as the other ingredients in the composition. The pharmaceutical compositions containing the erythropoietin glycoprotein products may be formulated at a strength effective for administration by various means to a human patient experiencing blood disorders characterized by low or defective red blood cell production. Average therapeutically effective amounts of the erythropoietin glycoprotein product may vary and in particular should be based upon the recommendations and prescription of a qualified physician.

The present invention is directed to erythropoietin glycoprotein products having the in vivo biological activity of causing bone marrow cells to increase production of reticulocytes and red blood cells represented by Formula 1:

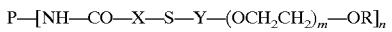

In Formula 1, P is an erythropoietin glycoprotein less the amino group or amino groups which form an amide linkage with X. As set out in detail below, the preparation and purification of EPO are well known in the art. By EPO is meant the natural or recombinant protein, preferably human, as obtained from any conventional source such as tissues, protein synthesis, cell culture with natural or recombinant cells. Any protein having the activity of EPO, such as muteins or otherwise modified proteins, is encompassed. Recombinant EPO may be prepared via expression in CHO—, BHK— or HeLa cell lines, by recombinant DNA technology or by endogenous gene activation. The preferred EPO species for the preparation of erythropoietin glycoprotein products are human EPO species. More preferably, the EPO species is the human EPO having the amino acid sequence set out in FIG. 1 (SEQ ID NO:1).

The human erythropoietin protein may also be modified at one or more additional sites for glycosylation such as, but not limited to, the amino acid sequences as set out below. The notation below means that the sequence set forth in FIG. 1 (SEQ ID NO:1) has been modified by substituting the native amino acid at the superscripted numbered position shown for the amino acid indicated to the left of the superscripted number.

Asn$^{30}$Thr$^{32}$ (SEQ ID NO:1);
Asn$^{51}$Thr$^{53}$ (SEQ ID NO:1);
Asn$^{57}$Thr$^{59}$ (SEQ ID NO:1);
Asn$^{69}$ (SEQ ID NO:1);
Asn$^{69}$Thr$^{71}$ (SEQ ID NO:1);
Ser$^{68}$Asn$^{69}$Thr$^{71}$ (SEQ ID NO:1);
Val$^{87}$Asn$^{88}$Thr$^{90}$ (SEQ ID NO: 1);
Ser$^{87}$Asn$^{88}$Thr$^{90}$ (SEQ ID NO:1);
Ser$^{87}$Asn$^{88}$Gly$^{89}$Thr$^{90}$ (SEQ ID NO:1);
Ser$^{87}$Asn$^{88}$Thr$^{90}$Thr$^{92}$ (SEQ ID NO:1);
Ser$^{87}$Asn$^{88}$Thr$^{90}$Ala$^{162}$ (SEQ ID NO:1);
ASn$^{69}$Thr$^{71}$Ser$^{87}$Asn$^{88}$Thr$^{90}$ (SEQ ID NO:1);
Asn$^{30}$Thr$^{32}$Val$^{87}$Asn$^{88}$Thr$^{90}$ (SEQ ID NO:1);
Asn$^{89}$Ile$^{90}$Thr$^{91}$ (SEQ ID NO:1);
Ser$^{87}$Asn$^{89}$Ile$^{90}$Thr$^{91}$ (SEQ ID NO:1);
Asn$^{136}$Thr$^{138}$ (SEQ ID NO:1);
Asn$^{138}$Thr$^{140}$ (SEQ ID NO:1);
Thr$^{125}$ (SEQ ID NO:1); and
Pro$^{124}$Thr$^{125}$ (SEQ ID NO:1).

The human erythropoietin protein may also be an analog having at least one additional amino acid at the carboxy terminal end of the glycoprotein, wherein the additional amino acid includes at least one glycosylation site. The at least one additional amino acid may comprise a peptide fragment derived from the carboxy terminal end of human chorionic gonadotropin. Preferably, the glycoprotein is an analog selected from the group consisting of (a) human erythropoietin having the amino acid sequence, Ser Ser Ser Ser Lys Ala Pro Pro Pro Ser Leu Pro Ser Pro Ser Arg Leu Pro Gly Pro Ser Asp Thr Pro Ile Leu Pro Gln (SEQ ID NO:3), extending from the carboxy terminus; (b) the analog in (a) further comprising $Ser^{87} Asn^{88} Thr^{90}$ EPO; and (c) the analog in (a) further comprising $Asn^{30} Thr^{32} Val^{87} Asn^{88} Thr^{90}$ EPO.

The human erythropoietin protein may also be an analog having an amino acid sequence which includes a rearrangement of at least one site for glycosylation. The rearrangement may comprise a deletion of any of the N-linked carbohydrate sites in human erythropoietin and an addition of an N-linked carbohydrate site at position 88 of the amino acid sequence of human erythropoietin. Preferably, the glycoprotein is an analog selected from the group consisting of $Gln^{24} Ser^{87} Asn^{88} Thr^{90}$ EPO; $Gln^{38} Ser^{87} Asn^{88} Thr^{90}$ EPO; and $Gln^{83} Ser^{87} Asn^{88} Thr^{90}$ EPO.

Erythropoietin analogs with additional glycosylation sites are disclosed in European Patent Publication No. 640 619, to Elliot, published Mar. 1, 1995, the contents of which are incorporated herein by reference.

In Formula 1, R may be any lower alkyl, by which is meant a linear or branched alkyl group having from one to six carbon atoms such as methyl, ethyl, isopropyl, etc. A preferred alkyl is methyl.

In Formula 1, X is $—(CH_2)_k—$ or $—CH_2(O—CH_2—CH_2)_k—$, wherein k is from 1 to about 10. Preferably, k is from 1 to about 4, more preferably, k is 1 or 2. Most preferably, X is $—(CH_2)$.

In Formula 1, Y is

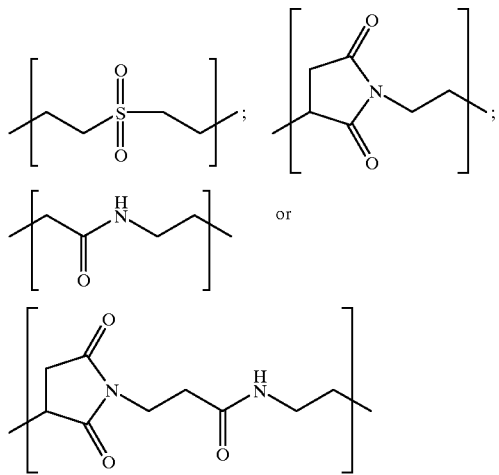

Preferably Y is

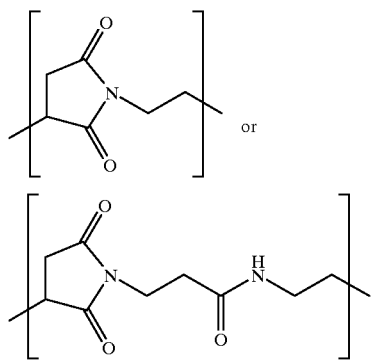

Most preferably, Y is

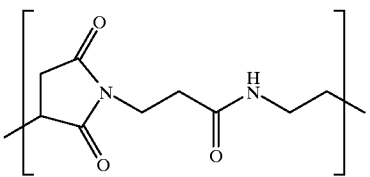

In Formula 1, the number m is selected such that the resulting conjugate of Formula 1 has a physiological activity comparable to unmodified EPO, which activity may represent the same as, more than, or a fraction of the corresponding activity of unmodified EPO. m represents the number of ethylene oxide residues in the PEG unit. A single PEG subunit of $—OCH_2CH_2—$ has a molecular weight of about 44 daltons. Thus, the molecular weight of the conjugate (excluding the molecular weight of the EPO) depends on the number m. A molecular weight of "about" a certain number means that it is within a reasonable range of that number as determined by conventional analytical techniques. m is an integer ranging from about 450 to about 900 (corresponding to a molecular weight of from 20 to 40 kDa), preferably m is from about 550 to about 800 (about 24 to 35 kDa), and most preferably m is from about 650 to about 700 (about 29 to about 31 kDa).

In Formula 1, the number n is the number of ε-amino groups of a lysine amino acid in an erythropoietin protein covalently bound to a PEG unit via an amide linkage. A conjugate of this invention may have one, two, or three PEG units per molecule of EPO. n is an integer ranging from 1 to 3, preferably n is 1 or 2, and more preferably n is 1.

Preferred erythropoietin glycoprotein products are represented by the formulae:

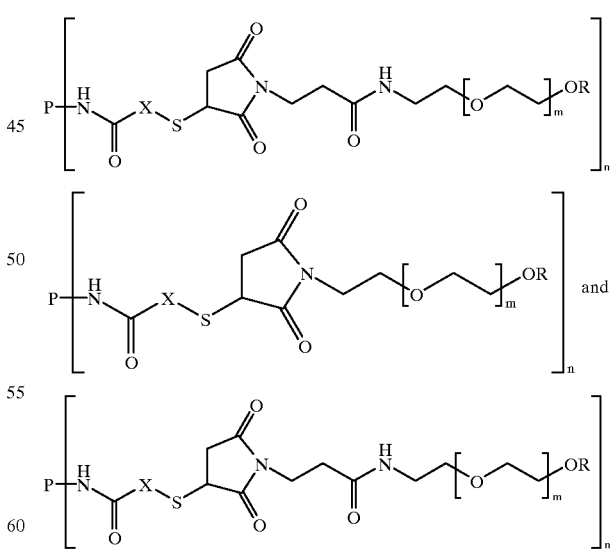

Most preferred erythropoietin glycoprotein products are represented by the formula:

Other preferred erythropoietin glycoprotein products are represented by the formulae:

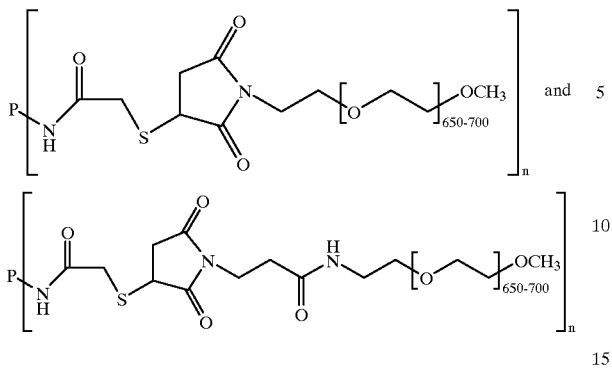

and

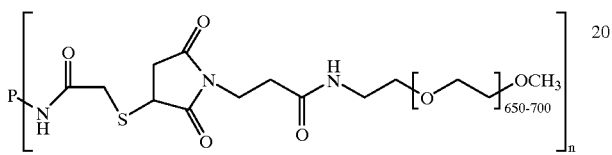

More preferred erythropoietin glycoprotein products are represented by the formula:

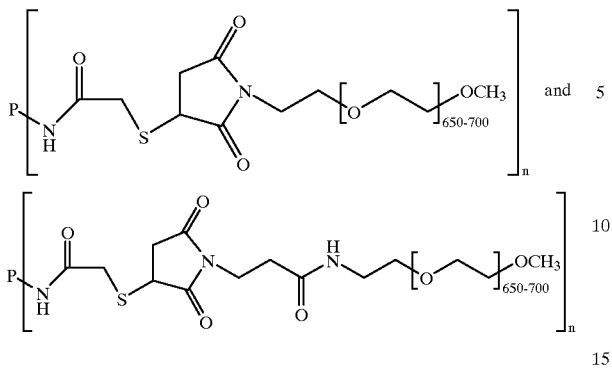

In another embodiment, the invention is directed to a method for the treatment of anemia in a human which comprises administering to a human a therapeutically effective amount of an erythropoietin glycoprotein product represented by Formula 1.

In still another embodiment, the invention is directed to a method for preparing an erythropoietin glycoprotein product, having the in vivo biological activity of causing bone marrow cells to increase production of reticulocytes and red blood cells, which comprises the steps of:

(a) covalently reacting an ε-amino group of a lysine amino acid of an erythropoietin protein represented by the formula, P—[NH$_2$]$_n$, with a bi-functional reagent represented by the formula, Z—CO—X—S—Q, to form an intermediate with an amide linkage represented by the formula:

P—[NH—CO—X—S—Q]$_n$ wherein P is an erythropoietin protein less the amino group which forms an amide linkage; n is an integer ranging from 1 to 3; Z is a reactive group, e.g. a carboxylic-NHS ester; X is —(CH$_2$)$_k$— or —CH$_2$(O—CH$_2$—CH$_2$)$_k$—, wherein k is from 1 to about 10; and Q is a protecting group, like alkanoyl, e.g. acetyl.

(b) covalently reacting the intermediate with an amide linkage from step (a) with an activated polyethylene glycol derivative represented by the formula, W—[OCH$_2$CH$_2$]$_m$—OR, to form an erythropoietin glycoprotein product represented by the formula:

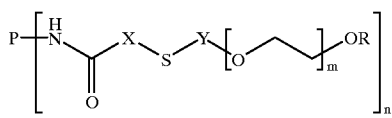

wherein W is a sulfhydryl reactive form of Y; m is an integer ranging from about 450 to about 900; R is lower alkyl; and Y is

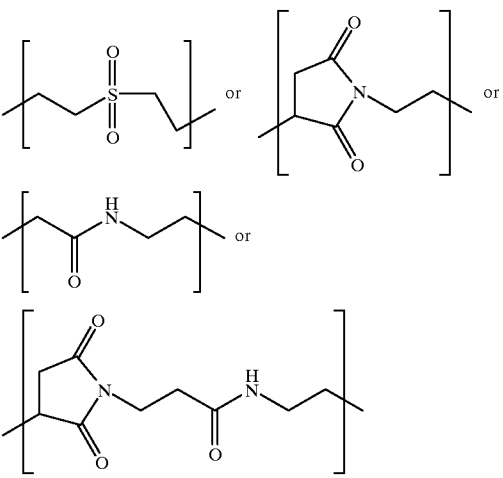

In this embodiment, the bi-functional reagent is preferably N-succinimidyl-S-acetylthiopropionate or N-succinimidyl-S-acetylthioacetate, Z is preferably N-hydroxy-succinimide, and the activated polyethylene glycol derivative W—[OCH$_2$CH$_2$]$_m$—OR is preferably selected from the group consisting of iodo-acetyl-methoxy-PEG, methoxy-PEG-vinylsulfone, and methoxy-PEG-maleimide.

Methods for Expressing EPO Proteins

Erythropoietin (EPO) is a human glycoprotein which stimulates the formation of erythrocytes. Its preparation and therapeutic application are described in detail for example in U.S. Pat. Nos. 5,547,933 and 5,621,080, EP-B 0 148 605, Huang, S. L., Proc. Natl. Acad. Sci. USA (1984) 2708–2712, EP-B 0 205 564, EP-B 0 209 539 and EP-B 0 411 678 as well as Lai, P. H. et al., J. Biol. Chem. 261 (1986) 3116–3121, an Sasaki, H. et al., J. Biol. Chem. 262 (1987) 12059–12076. Erythropoietin for therapeutic use may be produced by recombinant means (EP-B 0 148 605, EP-B 0 209 539 and Egrie, J. C., Strickland, T. W., Lane, J. et al. (1986) Immunobiol. 72: 213–224). Expression of proteins, including EPO, by endogenous gene activation is well known in the art and is disclosed, for example in U.S. Pat. Nos. 5,733,761, 5,641,670, and 5,733,746, and international patent publication Nos. WO 93/09222, WO 94/12650, WO 95/31560, WO 90/11354, WO 91/06667 and WO 91/09955, the contents of each of which are incorporated herein by reference.

Methods for the expression and preparation of erythropoietin in serum free medium are described for example in WO 96/35718, to Burg published Nov. 14, 1996, and in European Patent Publication No. 513 738, to Koch published Jun. 12, 1992.

Methods for Purifying Human EPO Protein

In addition to the references mentioned above, it is known that a serum-free fermentation of recombinant CHO cells which contain an EPO gene can be carried out. Such methods are described for example in EP-A 0 513 738, EP-A 0 267 678 and in a general form by Kawamoto, T. et al., Analytical Biochem. 130 (1983) 445–453, EP-A 0 248 656, Kowar, J. and Franek, F., Methods in Enzymology 421 (1986) 277–292, Bavister, B., Expcology 271 (1981) 45–51, EP-A 0 481 791, EP-A 0 307 247, EP-A 0 343 635, WO 88/00967.

In EP-A 0 267 678 an ion exchange chromatography on S-Sepharose, a preparative reverse phase HPLC on a C$_8$ column and a gel filtration chromatography are described for the purification of EPO produced in serum-free culture after dialysis. In this connection the gel filtration chromatography step can be replaced by ion exchange chromatography on S-Sepharose fast flow. It is also proposed that a dye chromatography on a Blue Trisacryl column be carried out before the ion exchange chromatography.

A process for the purification of recombinant EPO is described by Nobuo, I. et al., J. Biochem. 107 (1990) 352–359. In this process EPO is treated however with a solution of Tween® 20, phenylmethylsulfonyl fluoride, ethylmaleimide, pepstatin A, copper sulfate and oxamic acid prior to the purification steps.

Multiple references like WO 96/35718, to Burg published Nov. 14, 1996, discloses a process for preparing erythropoietin in a serum free fermentation process (EPOsf). One method to manufacture EPO as starting material for the pegylation is explained exemplary in the following.

Biological Assay for Determining Specific Activity of EPO and EPO Conjugates

The specific activity of EPO or EPO conjugates in accordance with this invention can be determined by various assays known in the art. The biological activity of the purified EPO proteins of this invention are such that administration of the EPO protein by injection to human patients results in bone marrow cells increasing production of reticulocytes and red blood cells compared to non-injected or control groups of subjects. The biological activity of the EPO proteins, or fragments thereof, obtained and purified in accordance with this invention can be tested by methods according to Pharm. Europa Spec. Issue Erythropoietin BRP Bio 1997(2).

Another biological assay for determining the activity of EPO protein, the normocythaemic mouse assay, is described in Example 4.

Processes for the Preparation of Pegylated EPO

Processes for the preparation of erythropoietin glycoprotein products represented by Formula 1 comprise the covalent linking of thiol groups to EPO ("activation") and coupling the resulting activated EPO with a poly(ethylene glycol) (PEG) derivative. The first step for the preparation of pegylated EPO according to the present invention comprises covalent linking of thiol groups via $NH_2$-groups of EPO. This activation of EPO is performed with bi-functional reagents which carry a protected thiol group and an additional reactive group, such as active esters (e.g., a succinimidylester), anhydrides, esters of sulphonic acids, halogenides of carboxylic acids and sulphonic acids, respectively. The thiol group is protected by groups known in the art, e.g., acetyl groups. These bi-functional reagents are able to react with the ξ-amino groups of the lysine amino acids by forming an amide linkage. The first step of the reaction is set out below:

EPO—[$NH_2$]$_n$ + [structure with Z—X—S—C(=O)CH$_3$] → EPO—[NH—C(=O)—X—S—C(=O)CH$_3$]$_n$ EPO, n and X are as defined above and Z is a reactive group known in the art, e.g. a N-hydroxy-succinimide (NHS) substituent of the formula

[NHS structure]

In a preferred embodiment the activation of the ε-amino lysine groups is performed by reaction with bi-functional reagents having a succinimidyl moiety. The bi-functional reagents may carry different spacer species, e.g. —(CH$_2$)$_k$— or —CH$_2$—(O—CH$_2$—CH$_2$—)$_k$— moities, wherein k is from 1 to about 10, preferably from 1 to about 4, and more preferably 1 or 2, and most preferably 1. Examples of these reagents are N-succinimidyl-S-acetylthiopropionate (SATP) and N-succinimidyl-S-acetylthioacetate (SATA)

[structure]

Acetylthioalkyl-carboxylic-NHS-ester, like

[SATP structure]

SATP

[SATA structure]

SATA

[2-(Acetylthio)-(ethoxy)$_k$-acetic-acid-NHS-ester structure]

2-(Acetylthio)-(ethoxy)$_k$-acetic-acid-NHS-ester with k as defined above.

The preparation of the bi-functional reagents is known in the art. Precursors of 2-(acetylthio)-(ethoxy)$_k$-acetic-acid-NHS-esters are described in DE-3924705, while the derivatization to the acetylthio compound is described by March, J., Advanced Organic Chemistry, McGraw-Hill, 1977, 375–376. SATA is commercially available (Molecular Probes, Eugene, OR, USA and Pierce, Rockford, Ill.).

The number of thiol groups to be added to an EPO molecule can be selected by adjusting the reaction parameters, i.e., the protein (EPO) concentration and the protein/bi-functional reagent ratio. Preferably, the EPO is activated by covalently linking from 1 to 5 thiol groups per EPO molecule, more preferably from 1.5 to 3 thiol groups per EPO molecule. These ranges refer to the statistical distribution of the thiol group over the EPO protein population.

The reaction is carried out, for example, in an aqueous buffer solution, pH 6.5–8.0, e.g., in 10 mM potassium phosphate, 50 mM NaCl, pH 7.3. The bi-functional reagent may be added in DMSO. After completion of the reaction, preferably after 30 minutes, the reaction is stopped by addition of lysine. Excess bifunctional reagent may be separated by methods known in the art, e.g., by dialysis or column filtration. The average number of thiol groups added to EPO can be determined by photometric methods described in, for example, Grasetti, D. R. and Murray, J. F. in J. Appl. Biochem. Biotechnol. 119, 41–49 (1967).

The above reaction is followed by covalent coupling of an activated polyethylene glycol (PEG) derivative. Suitable PEG derivatives are activated PEG molecules with an average molecular weight of from about 20 to about 40 kDa, more preferably from about 24 to about 35 kDa, and most preferably about 30 kDa.

Activated PEG derivatives are known in the art and are described in, for example, Morpurgo, M. et al. J. Bioconj. Chem. (1996) 7, page 363 ff for PEG-vinylsulfone. Linear chain and branched chain PEG species are suitable for the preparation of the compounds of Formula 1. Examples of reactive PEG reagents are iodo-acetyl-methoxy-PEG and methoxy-PEG-vinylsulfone: PEG-vinylsulfone:

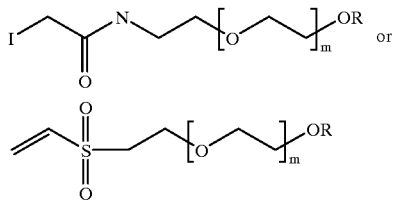

The use of these iodo-activated substances is known in the art and described e.g. by Hermanson, G. T. in Bioconjugate Techniques, Academic Press, San Diego (1996) p. 147–148.

Most preferably, the PEG species are activated by maleimide using (alkoxy-PEG-maleimide), such as methoxy-PEG-maleimide (MW 30000; Shearwater Polymers, Inc.). The structure of alkoxy-PEG-maleimide is as follows:

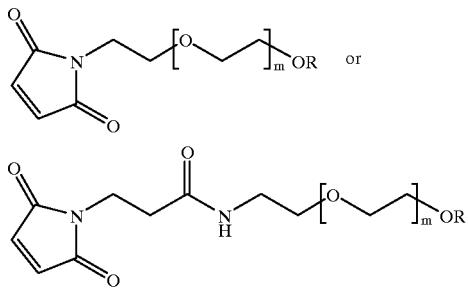

with R and m are as defined above.

The most preferred derivative is

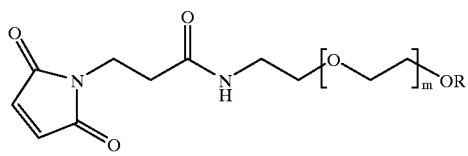

The coupling reaction with alkoxy-PEG-maleimide takes place after in situ cleavage of the thiol protecting group in an aqueous buffer solution, e.g. 10 mM potassium phosphate, 50 mM NaCl, 2 mM EDTA, pH 6.2. The cleavage of the protecting group may be performed, for example, with hydroxylamine in DMSO at 25° C., pH 6.2 for about 90 minutes. For the PEG modification the molar ratio of activated EPO/alkoxy-PEG-maleimide should be from about 1:3 to about 1:6, and preferably 1:4. The reaction may be stopped by addition of cysteine and reaction of the remaining thiol (—SH) groups with N-methylmaleimide or other appropriate compounds capable of forming disulfide bonds. Because of the reaction of any remaining active thiol groups with a protecting group such as N-methylmaleimide or other suitable protecting group, the EPO glycoproteins in the conjugates of this invention may contain such protecting groups. Generally the procedure described herein will produce a mixture of molecules having varying numbers of thiols protected by different numbers of the protecting group, depending on the number of activated thiol groups on the glycoprotein that were not conjugated to PEG-maleimide.

Whereas N-methylmaleimide forms the same type of covalent bond when used to block the remaining thiol-groups on the pegylated protein, disulfide compounds will lead in an intermolecular sulfide/disulfide exchange reaction to a disulfide bridged coupling of the blocking reagent. Preferred blocking reagents for that type of blocking reaction are oxidized glutathione (GSSG), cysteine and cystamine. Whereas with cysteine no additional net charge is introduced into the pegylated protein, the use of the blocking reagents GSSG or cystamine results in an additional negative or positive charge.

The further purification of the compounds of Formula 1, including the separation of mono-, di- and tri-pegylated EPO species, may be done by methods known in the art, e.g., column chromatography.

Pharmaceutical Compositions

The erythropoietin glycoprotein products prepared in accordance with this invention may be prepared in pharmaceutical compositions suitable for injection with a pharmaceutically acceptable carrier or vehicle by methods known in the art.

Treating Blood Disorders Characterized by Low or Defective Red Blood Cell Production Administration of the erythropoietin glycoprotein products of the present invention results in red blood cell formation in humans. Therefore, administration of the erythropoietin glycoprotein products replenishes this EPO protein which is important in the production of red blood cells. The pharmaceutical compositions containing the erythropoietin glycoprotein products may be formulated at a strength effective for administration by various means to a human patient experiencing blood disorders characterized by low or defective red blood cell production, either alone or as part condition or disease. The pharmaceutical compositions may be administered by injection such as by subcutaneous or intravenous injection. Average quantities of the erythropoietin glycoprotein product may vary and in particular should be based upon the recommendations and prescription of a qualified physician.

Throughout this application, various publications have been referenced. The disclosures in these publications are incorporated herein by reference in order to describe more fully the state of the art.

The present invention is further illustrated by the following examples which are presented for purposes of demonstrating, but not limiting, the preparation of the compounds and compositions of this invention.

EXAMPLE 1
Fermentation and Purification of Human EPO
a) Inoculum Preparation and Fermentation One vial of the Working Cell Bank, originating from an EPO-producing CHO cell line (ATCC CRL8695, disclosed in EP 411 678 (Genetics Institute) can be used) is taken from the gas phase of the liquid nitrogen storage tank. The cells are transferred into glass spinner flasks and cultivated in a hydrogen carbonate-buffered medium in a humidified $CO_2$ incubator. Typical serum free media used for the inoculum preparation and fermentation are disclosed in European Patent Application 513 738, to Koch published Jun. 12, 1992, or WO 96/35718, to Burg published Nov. 14, 1996, for example contain as medium DMEM/F12 (e.g. JRH Biosciences/Hazleton Biologics, Denver, US, order No. 57-736) and additionally sodium hydrogencarbonate, L+glutamine, D+glucose, recombinant insulin, sodium selenite, diaminobutane, hydrocortisone, iron(II) sulfate, asparagine, aspartic acid, serine and a stabilizer for mammalian cells such as e.g. polyvinyl alcohol, methyl cellulose, polydextran, polyethylene glycol, Pluronic F68, plasma expander polygelin (HEMACCEL®) or polyvinyl pyrrolidone (WO 96/35718).

The cultures are microscopically checked for the absence of contaminating microorganisms, and the cell densities are determined. These tests are performed at each splitting step.

After the initial growth period, the cell culture is diluted with fresh medium to the starting cell density and undergoes another growth cycle. This procedure is repeated until a culture volume of approximately 2 l per glass spinner flask has been obtained. After approx. 12 doublings 1 to 5 liter of this culture is available which then is used as inoculum for the 10 l inoculum fermenter.

After 3–5 days, the culture in the 10 l fermenter can be used as inoculum for the 100 l inoculum fermenter.

After additional 3–5 days of cultivation, the culture in the 100 l fermenter can be used as inoculum for the 1000 l production fermenter.

b) Harvesting and Cell Separation

A batch refeed process is used, i.e. when the desired cell density is reached, approx. 80% of the culture is harvested. The remaining culture is replenished with fresh culture medium and cultivated until the next harvest. One production run consists of a maximum of 10 subsequent harvests: 9 partial harvests and 1 overall harvest at the end of fermentation. Harvesting takes place every 3–4 days.

The determined harvest volume is transferred into a cooled vessel. The cells are removed by centrifugation or filtration and discarded. The EPO containing supernatant of the centrifugation step is in-line filtered and collected in a second cooled vessel. Each harvest is processed separately during purification.

A typical process for the purification of EPO-protein is disclosed in WO 96/35718, to Burg published Nov. 14, 1996. The purification process is explained exemplary in the following.

a) Blue Sepharose Chromatography

Blue Sepharose (Pharmacia) consists of Sepharose beads to the surface of which the Cibacron blue dye is covalently bound. Since EPO binds more strongly to Blue Sepharose than most non-proteinaceous contaminants, some proteinaceous impurities and PVA, EPO can be enriched in this step. The elution of the Blue Sepharose column is performed by increasing the salt concentration as well as the pH.

The column is filled with 80–100 l of Blue Sepharose, regenerated with NaOH and equilibrated with equilibration buffer (sodium/calcium chloride and sodium acetate). The acidified and filtered fermenter supernatant is loaded. After completion of the loading, the column is washed first with a buffer similar to the equilibration buffer containing a higher sodium chloride concentration and consecutively with a Tris-base buffer. The product is eluted with a Tris-base buffer and collected in a single fraction in accordance with the master elution profile.

b) Butyl Toyopearl Chromatography

The Butyl Toyopearl 650 C (TosoHaas) is a polystyrene based matrix to which aliphatic butyl-residues are covalently coupled. Since EPO binds more strongly to this gel than most of the impurities and PVA, it has to be eluted with a buffer containing isopropanol.

The column is packed with 30–40 l of Butyl Toyopearl 650 C, regenerated with NaOH, washed with a Tris-base buffer and equilibrated with a Tris-base buffer containing isopropanol.

The Blue Sepharose eluate is adjusted to the concentration of isopropanol in the column equilibration buffer and loaded onto the column. Then the column is washed with equilibration buffer with increased isopropanol concentration. The product is eluted with elution buffer (Tris-base buffer with high isopropanol content) and collected in a single fraction in accordance with the master elution profile.

c) Hydroxyapatite Ultrogel Chromatography

The Hydroxyapatite Ultrogel (Biosepra) consists of hydroxyapatite which is incorporated in an agarose matrix to improve the mechanical properties. EPO has a low affinity to hydroxyapatite and can therefore be eluted at lower phosphate concentrations than protein impurities.

The column is filled with 30–40 l of Hydroxyapatite Ultrogel and regenerated with a potassium phosphate/calcium chloride buffer and NaOH followed by a Tris-base buffer. Then it is equilibrated with a Tris-base buffer containing a low amount of isopropanol and sodium chloride.

The EPO containing eluate of the Butyl Toyopearl chromatography is loaded onto the column. Subsequently the column is washed with equilibration buffer and a Tris-base buffer without isopropanol and sodium chloride. The product is eluted with a Tris-base buffer containing a low concentration of potassium phosphate and collected in a single fraction in accordance with the master elutiogram.

d) Reversed Phase HPLC on Vydac C4

The RP-HPLC material Vydac C4 (Vydac) consists of silica gel particles, the surfaces of which carry C4-alkyl chains. The separation of EPO from the proteinaceous impurities is based on differences in the strength of hydrophobic interactions. Elution is performed with an acetonitrile gradient in diluted trifluoroacetic acid.

Preparative HPLC is performed using a stainless steel column (filled with 2.8 to 3.2 liter of Vydac C4 silicagel). The Hydroxyapatite Ultrogel eluate is acidified by adding trifluoro-acetic acid and loaded onto the Vydac C4 column. For washing and elution an acetonitrile gradient in diluted trifluoroacetic acid is used. Fractions are collected and immediately neutralized with phosphate buffer. The EPO fractions which are within the IPC limits are pooled.

e) DEAE Sepharose Chromatography

The DEAE Sepharose (Pharmacia) material consists of diethylaminoethyl (DEAE)-groups which are covalently bound to the surface of Sepharose beads. The binding of EPO to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and EPO is eluted with a buffer with increased ionic strength.

The column is packed with DEAE Sepharose fast flow. The column volume is adjusted to assure an EPO load in the range of 3–10 mg EPO/ml gel. The column is washed with water and equilibration buffer (sodium/ potassium phosphate). The pooled fractions of the HPLC eluate are loaded and the column is washed with equilibration buffer. Then the column is washed with washing buffer (sodium acetate buffer) followed by washing with equilibration buffer. Subsequently, EPO is eluted from the column with elution buffer (sodium chloride, sodium/potassium phosphate) and collected in a single fraction in accordance with the master elution profile.

The eluate of the DEAE Sepharose column is adjusted to the specified conductivity. The resulting drug substance is sterile filtered into Teflon bottles and stored at −70° C.

EXAMPLE 2
Covalent Linking of Thiol Groups to EPO

This example discloses the determination of reaction conditions for the covalent linking of thiol groups to EPO. To determine the conditions, different amounts of a reagent containing a blocked thiol group, here SATA or SATP (dissolved in DMSO ad 10 mg/ml) were added to the EPO solution, here to 1 ml of 5 mg/ml EPO in 10 mM potassium phosphate, 50 mM NaCl, pH 7.3. The reaction was stirred for about 30 minutes (25° C.) and stopped by addition of 1 M lysine solution at 10 mM. Excess amounts of SATA and SATP were removed by dialysis against 10 mM potassium phosphate, 50 mM NaCl and 2 mM EDTA, pH 6.2. After removal of the protecting acetyl group with hydroxylamine, the number of thiol groups covalently linked to EPO was determined photometrically with dithiodipyridine according to the method described by Grasetti, D. R. and Murray, J. F. in J. Appl. Biochem. Biotechnol. 119, page 41–49 (1967).

The number of thiol groups covalently linked per EPO molecule is shown below.

| Molar ratio EPO: SATA or SATP | Mol thiol groups/ mol EPO |
| --- | --- |
| EPO:SATA = 1:3 | 1.5 |
| EPO:SATA = 1:5 | 2.4 |
| EPO:SATA = 1:6 | 3.2 |
| EPO:SATP = 1:3 | 1.3 |
| EPO:SATP = 1:4 | 2.5 |
| EPO:SATP = 1:6 | 3.7 |

EXAMPLE 3
Modification of Activated EPO with Methoxy-PEG-maleimide

A) Activation of EPO 100 mg EPO produced according to Example 1 (190,000 IU/mg as determined by the normocythaemic mouse assay) were activated with SATA (molar ratio: EPO/SATA=1/5) according to Example 2. The resulting EPO ("activated EPO") carrying covalently linked blocked thiol groups was separated from by-products like N-hydroxy-succinimide or non-reacted SATA by dialysis as described in Example 1. A solution of 4.5 mg/ml activated EPO in 10 mM potassium phosphate, 50 mM NaCl, 2 mM EDTA, pH 6.2 was obtained.

B) Pegylation of Activated EPO 380 mg methoxy-PEG-maleimide having the "most preferred" structure illustrated above (MW 30.000; Shearwater Polymers, Inc., Huntsville (Ala., USA)) was dissolved in the above solution containing 95 mg activated EPO (4.5 mg/ml in 10 mM potassium phosphate, 50 mM NaCl, 2 mM EDTA, pH 6.2). The resulting molar ratio between activated EPO and methoxy-PEG-maleimide in the solution was 1:4. By addition of 1 M aqueous hydroxylamine solution ad 30 mM, pH 6.2 to the above solution the covalently linked blocked thiol groups of activated EPO were de-blocked. The resulting activated EPO in the reaction mixture of the solution contained free thiol (—SH) groups. De-blocking of the thiol groups was followed immediately by the coupling reaction between the activated EPO now containing free thiol (—SH) groups and methoxy-PEG-maleimide for 90 minutes (stirring, 25° C.). The coupling reaction was stopped by addition of 0.2 M aqueous cysteine solution ad 2 mM to the reaction mixture. After 30 minutes excess free thiol groups of the activated EPO which did not react with methoxy-PEG-maleimide were blocked by addition of a 0.5 M N-methylmaleimide solution in DMSO to reach a concentration of 5 mM. After 30 minutes the resulting reaction mixture now containing pegylated EPO species was dialyzed against 10 mM potassium phosphate, pH 7.5 for ≧15 hours.

C) Purification of Pegylated EPO Species

For separation of the pegylated EPO species from the reaction mixture, the following purification process was performed: A 50 ml Q-Sepharose ff column was equilibrated with 10 mM potassium phosphate, pH 7.5. The reaction mixture obtained in step B) was loaded onto the column (flow rate: 3 column volumes (CV) per hour). In order to separate non-reacted methoxy-PEG-maleimide reagent, the column was washed with 5 CV's of 10 mM potassium phosphate, pH 7.5. Pegylated EPO species were separated by elution with an increasing salt gradient consisting of 5 CV's buffer A (10 mM potassium phosphate, pH 7.5) and 5 CV's buffer B (10 mM potassium phosphate, 500 mM NaCl, pH 7.5) with a flow rate of 3 CV per hour. Based on the NaCl gradient, the pegylated EPO species (tri-, bi- and mono-pegylated EPO species) were eluted first, followed by the non-pegylated EPO species. The fraction of the eluate containing the pegylated EPO species (tri-, di- and mono-pegylated EPO species) was pooled and filtered (sterile filtration with a 0.2 μm filter).

Content and purity of tri-, di- and mono-pegylated EPO species were evaluated on Coomassie-stained SDS-PAA gels (Laemmli, Nature 227, 680–685 (1970)) while protein concentrations were measured at 280 nm according the Beer-Lambert law. The apparent molecular weights of the EPO species determined by SDS-PAA electrophoresis were about 68 kDa (mono-pegylated EPO species), about 98 kDa (di-pegylated EPO species), and about 128 kDa (tri-pegylated EPO species).

Further separation of the tri-, di and mono-pegylated EPO species can be achieved by chromatography, e.g. by size exclusion chromatography (Superdex, pg 200; Pharmacia).

The determination of in-vivo biological activity of the eluate containing tri- di- and mono-pegylated species was performed by the method described in Example 4.

EXAMPLE 4
In-vivo Activity of Pegylated EPO Determined by the Normocythaemic Mouse Assay The normocythaemic mouse bioassay is known in the art (Pharm. Europa Spec. Issue Erythropoietin BRP Bio 1997 (2)) and a method in the monography of erythropoietin of Ph. Eur. BRP. The samples are diluted with BSA-PBS. Normal healthy mice, 7–15 weeks old, are administered s.c. 0.2 ml of the EPO-fraction containing tri-, di- and mono-pegylated EPO as described in Example 2. Over a period of 4 days starting 72 hours after the administration, blood is drawn by puncture of the tail vein and diluted such that 1 μl of blood is present in 1 ml of an 0.15 μmol acridine orange staining solution. The staining time is 3 to 10 minutes. The reticulocyte counts are carried out microfluorometrically in a flow cytometer by analysis of the red fluorescence histogram. The reticulocyte counts are given in terms of absolute figures (per 30,000 blood cells analyzed). For the data presented, each group consisted of 5 mice per day, and the mice were bled only once.

Methoxy-PEG-maleimide coupled to EPO according to Example 3, unmodified EPO and buffer solution were administered to mice. The results are shown in FIG. 3. The results show the superior activity and the prolonged half life of the pegylated EPO species indicated by the significantly increased amounts of reticulocytes and the shift of the reticulocytes count maxiumum using the same dose per mouse.

What is claimed is:

1. A conjugate, said conjugate comprising an erythropoietin glycoprotein having at least one free amino group and having the in vivo biological activity of causing bone marrow cells to increase production of reticulocytes and red blood cells and selected from the group consisting of human erythropoietin and analogs thereof which have the primary structure of human erythropoietin modified by the addition of from 1 to 6 glycosylation sites or by the rearrangement of at least one glycosylation site; said glycoprotein being covalently linked to from one to three lower-alkoxy poly(ethylene glycol) groups, each poly(ethylene glycol) group being covalently linked to the glycoprotein via a linker of the formula —C(O)—X—S—Y— with the C(O) of the linker forming an amide bond with one of said amino groups, X is —CH$_2$)$_k$— or —CH$_2$(O—CH$_2$—CH$_2$)$_k$—, k is from 1 to 10, Y is

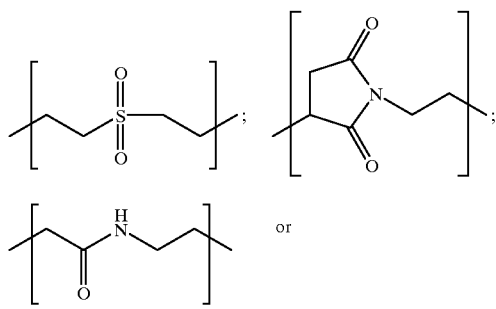

or

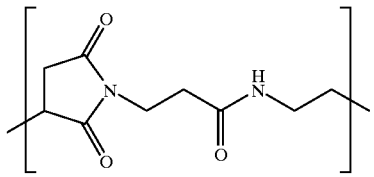

the average molecular weight of each poly(ethylene glycol) group is from about 20 kilodaltons to about 40 kilodaltons, and the molecular weight of the conjugate is from about 51 kilodaltons to about 175 kilodaltons.

2. The conjugate of claim 1, wherein the erythropoietin glycoprotein is a human erythropoietin protein.

3. The conjugate of claim 2, wherein the human erythropoietin protein is expressed by endogenous gene activation.

4. The conjugate of claim 2, wherein the erythropoietin glycoprotein has the amino acid sequence set out in (SEQ ID NO:1) or (SEQ ID NO:2).

5. The conjugate of claim 4, wherein X is —(CH$_2$)$_k$—.

6. The conjugate of claim 4, wherein k is from 1 to 4.

7. The conjugate of claim 4, wherein the average molecular weight of each poly(ethylene glycol) group is from about 24 kilodaltons to about 35 kilodaltons.

8. The conjugate of claim 7, wherein the average molecular weight of each poly(ethylene glycol) group is about 30 kilodaltons.

9. The conjugate of claim 4, wherein the glycoprotein is covalently linked to one or two lower-alkoxy capped poly(ethylene glycol) groups.

10. The conjugate of claim 4, wherein the poly(ethylene glycol) groups are capped by methoxy.

11. The conjugate of claim 2, of the formula:

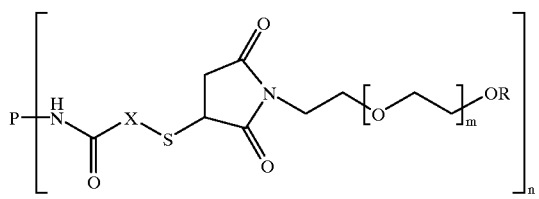

wherein n is an integer from 1 to 3; m is an integer from 450 to 900; R is lower alkyl; X is —(CH$_2$)$_k$— or —CH$_2$(O—CH$_2$—CH$_2$)$_k$—, and P is the residue of the erythropoietin glycoprotein without the amino group or groups which form an amide linkage with X.

12. The conjugate of claim 11, wherein X is —CH$_2$—.

13. The conjugate of claim 11, wherein m is an integer from 550 to 800.

14. The conjugate of claim 13, wherein m is an integer from 650 to 700.

15. The conjugate of claim 11, wherein n is 1.

16. The conjugate of claim 11, wherein R is methyl.

17. The conjugate of claim 11, wherein P has the amino acid sequence set out in (SEQ ID NO:1) or (SEQ ID NO:2).

18. The conjugate of claim 2, of the formula:

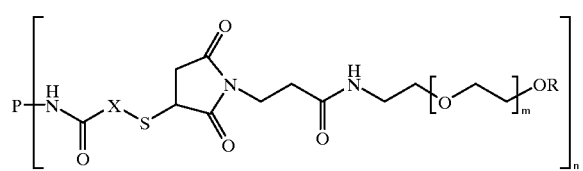

wherein n is an integer from 1 to 3; m is an integer from 450 to 900; R is lower alkyl; X is —(CH$_2$)$_k$— or —CH$_2$(O—CH$_2$—CH$_2$)$_k$—, and P is the residue of the erythropoietin glycoprotein without the amino group or groups which form an amide linkage with X.

19. The conjugate of claim 18, wherein X is —CH$_2$—.

20. The conjugate of claim 18, wherein m is an integer from 550 to 800.

21. The conjugate of claim 20, wherein m is an integer from 650 to 700.

22. The conjugate of claim 18, wherein R is methyl.

23. The conjugate of claim 18, wherein P has the amino acid sequence set out in (SEQ ID NO:1) or (SEQ ID NO:2).

24. The conjugate of claim 1, wherein the erythropoietin glycoprotein has the primary structure of human erythropoietin modified by the addition of from 1 to 6 glyosylation sites.

25. The conjugate of claim 1, wherein the glycoprotein has a sequence selected from the group consisting of:

Asn$^{30}$Thr$^{32}$ (SEQ ID NO:1);
Asn$^{51}$Thr$^{53}$ (SEQ ID NO:1),
Asn$^{57}$Thr$^{59}$ (SEQ ID NO:1);
Asn$^{69}$(SEQ ID NO:1);
Asn$^{69}$Thr$^{71}$ (SEQ ID NO:1);
Ser$^{68}$Asn$^{69}$Thr$^{71}$ (SEQ ID NO:1);
Val$^{87}$Asn$^{88}$Thr$^{90}$ (SEQ ID NO:1);
Ser$^{87}$Asn$^{88}$Thr$^{90}$ (SEQ ID NO:1);
Ser$^{87}$Asn$^{88}$Gly$^{89}$Thr$^{90}$ (SEQ ID NO:1);
Ser$^{87}$Asn$^{88}$Thr$^{90}$Thr$^{92}$ (SEQ ID NO:1);
Ser$^{87}$Asn$^{88}$Thr$^{90}$Ala$^{162}$ (SEQ ID NO:1);
Asn$^{69}$Thr$^{71}$Ser$^{87}$Asn$^{88}$Thr$^{90}$ (SEQ ID NO:1);
Asn$^{30}$Thr$^{32}$Val$^{87}$Asn$^{88}$Thr$^{90}$ (SEQ ID NO:1);
Asn$^{89}$Ile$^{90}$Thr$^{91}$(SEQ ID NO:1);
Ser$^{87}$Asn$^{89}$Ile$^{90}$Thr$^{91}$ (SEQ ID NO:1);
Asn$^{136}$Thr$^{138}$ (SEQ ID NO:1);
Asn$^{138}$Thr$^{140}$ (SEQ ID NO:1);
Thr$^{125}$ (SEQ ID NO:1); and
Pro$^{124}$Thr$^{125}$ (SEQ ID NO:1).

26. The conjugate of claim 25, wherein X is —(CH$_2$)$_k$—.

27. The conjugate of claim 25, wherein k is from 1 to 4.

28. The conjugate of claim 25, wherein the average molecular weight of each poly(ethylene glycol) group is from about 24 kilodaltons to about 35 kilodaltons.

29. The conjugate of claim 28, wherein the average molecular weight of each poly(ethylene glycol) group is about 30 kilodaltons.

30. The conjugate of claim 25, wherein the glycoprotein is covalently linked to one or two lower-alkoxy capped poly(ethylene glycol) groups.

31. The conjugate of claim 25, wherein the poly(ethylene glycol) groups are capped by methoxy.

32. The conjugate of claim 25, of the formula:

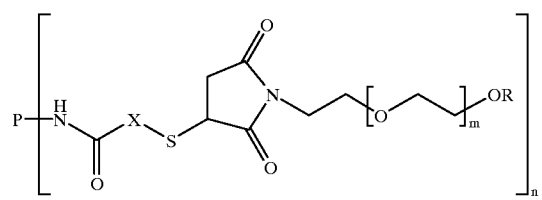

wherein n is an integer from 1 to 3; m is an integer from 450 to 900; R is lower alkyl; X is —(CH$_2$)$_k$— or —CH$_2$(O—CH$_2$—CH$_2$)$_k$—, and P is the residue of the erythropoietin glycoprotein without the amino group or groups which form an amide linkage with X.

33. The conjugate of claim 32, wherein X is —CH$_2$—.

34. The conjugate of claim 32, wherein m is an integer from 550 to 800.

35. The conjugate of claim 34, wherein m is an integer from 650 to 700.

36. The conjugate of claim 32, wherein n is 1.

37. The conjugate of claim 32, wherein R is methyl.

38. The conjugate of claim 25, of the formula:

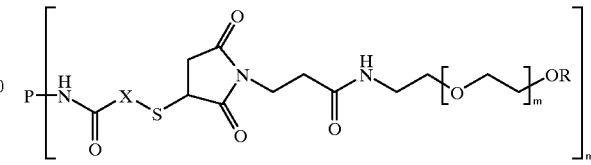

wherein n is an integer from 1 to 3; m is an integer from 450 to 900; R is lower alkyl; X is —(CH$_2$)$_k$— or —CH$_2$(O—CH$_2$—CH$_2$)$_k$—, and P is the residue of the erythropoietin glycoprotein without the amino group or groups which form an amide linkage with X.

39. The conjugate of claim 38, wherein X is —CH$_2$—.

40. The conjugate of claim 38, wherein m is an integer from 550 to 800.

41. The conjugate of claim 40, wherein m is an integer from 650 to 700.

42. The conjugate of claim 38, wherein R is methyl.

43. The conjugate of claim 1, wherein the glycoprotein has a sequence comprising the sequence of human erythropoietin and a second sequence at the carboxy terminus of the human erythropoietin sequence, wherein the second sequence contains at least one glycosylation site.

44. The conjugate of claim 43, wherein the second sequence comprises a sequence derived from the carboxy terminal sequence of human chorionic gonadotropin.

45. The conjugate of claim 44, wherein the glycoprotein has a sequence selected from the group consisting of:
  (a) the sequence of human erythropoietin and the sequence (SEQ ID NO:3) at the carboxy terminus of the human erythropoietin sequence;
  (b) the sequence in (a) modified by $Ser^{87} Asn^{88} Thr^{90}$; and
  (c) the sequence in (a) modified by $Asn^{30} Thr^{32} Val^{87} Asn^{88} Thr^{90}$.

46. The conjugate of claim 45, wherein X is $-(CH_2)_k-$.

47. The conjugate of claim 45, wherein k is from 1 to 4.

48. The conjugate of claim 45, wherein the average molecular weight of each poly(ethylene glycol) group is from about 24 kilodaltons to about 35 kilodaltons.

49. The conjugate of claim 48, wherein the average molecular weight of each poly(ethylene glycol) group is about 30 kilodaltons.

50. The conjugate of claim 45, wherein the glycoprotein is covalently linked to one or two lower-alkoxy capped poly(ethylene glycol) groups.

51. The conjugate of claim 45, wherein the poly(ethylene glycol) groups are capped by methoxy.

52. The conjugate of claim 45, of the formula:

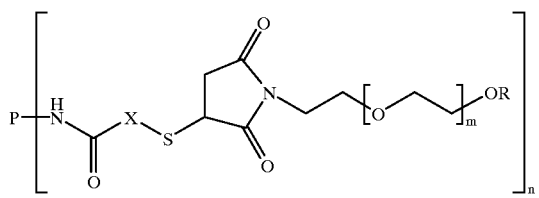

wherein n is an integer from 1 to 3; m is an integer from 450 to 900; R is lower alkyl; X is $-(CH_2)_k-$ or $-CH_2(O-CH_2-CH_2)_k-$, and P is the residue of the erythropoietin glycoprotein without the amino group or groups which form an amide linkage with X.

53. The conjugate of claim 52, wherein X is $-CH_2-$.

54. The conjugate of claim 52, wherein m is an integer from 550 to 800.

55. The conjugate of claim 54, wherein m is an integer from 650 to 700.

56. The conjugate of claim 52, wherein n is 1.

57. The conjugate of claim 52, wherein R is methyl.

58. The conjugate of claim 52, wherein the sequence of human erythropoietin is the sequence set out in (SEQ ID NO:1) or (SEQ ID NO:2).

59. The conjugate of claim 45, of the formula:

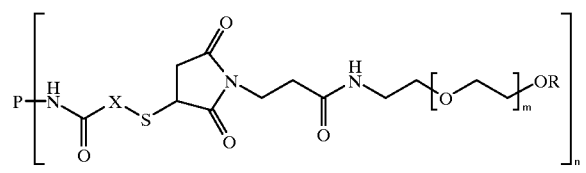

wherein n is an integer from 1 to 3; m is an integer from 450 to 900; R is lower alkyl; X is $-(CH_2)_k-$ or $-CH_2(O-CH_2-CH_2)_k-$, and P is the residue of the erythropoietin glycoprotein without the amino group or groups which form an amide linkage with X.

60. The conjugate of claim 59, wherein X is $-CH_2-$.

61. The conjugate of claim 59, wherein m is an integer from 550 to 800.

62. The conjugate of claim 61, wherein m is an integer from 650 to 700.

63. The conjugate of claim 59, wherein R is methyl.

64. The conjugate of claim 59, wherein the sequence of human erythropoietin is the sequence set out in (SEQ ID NO:1) or (SEQ ID NO:2).

65. The conjugate of claim 1, wherein the glycoprotein has the sequence of human erythropoietin modified by a rearrangement of at least one glycosylation site.

66. The conjugate of claim 65, wherein the rearrangement comprises deletion of any of the N-linked glycosylation sites in human erythropoietin and addition of an N-linked glycosylation site at position 88 of the sequence of human erythropoietin.

67. The conjugate of claim 66, wherein the glycoprotein has the sequence of human erythropoietin modified by a modification selected from the group consisting of:

$Gln^{24} Ser^{87} Asn^{88} Thr^{90}$;

$Gln^{38} Ser^{87} Asn^{88} Thr^{90}$; and $Gln^{83} Ser^{87} Asn^{88} Thr^{90}$.

68. The conjugate of claim 67, wherein X is $-(CH_2)_k-$.

69. The conjugate of claim 67, wherein k is from 1 to 4.

70. The conjugate of claim 67, wherein the average molecular weight of each poly(ethylene glycol) group is from about 24 kilodaltons to about 35 kilodaltons.

71. The conjugate of claim 70, wherein the average molecular weight of each poly(ethylene glycol) group is about 30 kilodaltons.

72. The conjugate of claim 67, wherein the glycoprotein is covalently linked to one or two lower-alkoxy capped poly(ethylene glycol) groups.

73. The conjugate of claim 67, wherein the poly(ethylene glycol) groups are capped by methoxy.

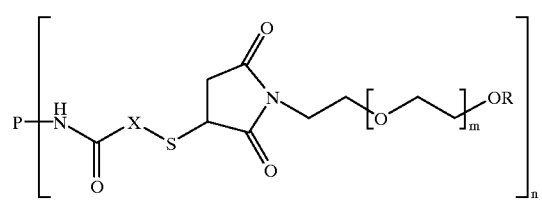

74. The conjugate of claim 67, of the formula:

wherein n is an integer from 1 to 3; m is an integer from 450 to 900; R is lower alkyl; X is $-(CH_2)_k-$ or $-CH_2(O-CH_2-CH_2)_k-$, and P is the residue of the erythropoietin glycoprotein without the amino group or groups which form an amide linkage with X.

75. The conjugate of claim 74, wherein X is $-CH_2-$.

76. The conjugate of claim 74, wherein m is an integer from 550 to 800.

77. The conjugate of claim 76, wherein m is an integer from 650 to 700.

78. The conjugate of claim 74, wherein n is 1.

79. The conjugate of claim 74, wherein R is methyl.

80. The conjugate of claim 67, of the formula:

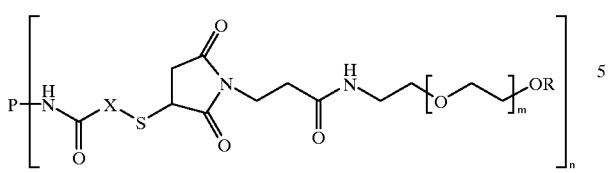

wherein n is an integer from 1 to 3; m is an integer from 450 to 900; R is lower alkyl; X is —(CH$_2$)$_k$— or —CH$_2$(O—CH$_2$—CH$_2$)$_k$—, and P is the residue of the erythropoietin glycoprotein without the amino group or groups which form an amide linkage with X.

81. The conjugate of claim 80, wherein X is —CH$_2$—.

82. The conjugate of claim 80, wherein m is an integer from 550 to 800.

83. The conjugate of claim 82, wherein m is an integer from 650 to 700.

84. The conjugate of claim 80, wherein R is methyl.

85. A composition comprising conjugates, each of said conjugates comprising an erythropoietin glycoprotein having at least one free amino group and having the in vivo biological activity of causing bone marrow cells to increase production of reticulocytes and red blood cells and selected from the group consisting of human erythropoietin and analogs thereof which have the primary structure of human erythropoietin modified by the addition of from 1 to 6 glycosylation sites or by the rearrangement of at least one glycosylation site; said glycoprotein being covalently linked to from one to three lower-alkoxy poly(ethylene glycol) groups, each poly(ethylene glycol) group being covalently linked to the glycoprotein via a linker of the formula —C(O)—X—S—Y— with the C(O) of the linker forming an amide bond with one of said amino groups, X is —(CH$_2$ )$_k$— or —CH$_2$(O—CH$_2$—CH$_2$)$_k$—, k is from 1 to 10, Y is

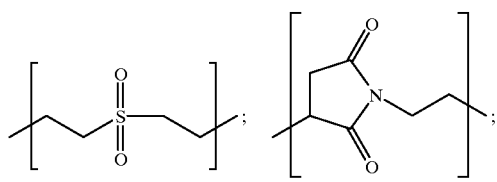

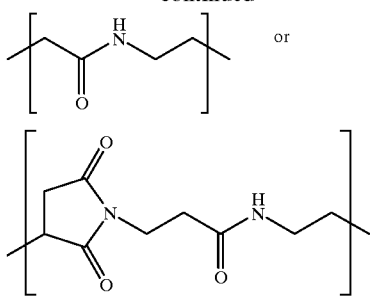

the average molecular weight of each poly(ethylene glycol) group is from about 20 kilodaltons to about 40 kilodaltons, and the molecular weight of the conjugate is from about 51 kilodaltons to about 175 kilodaltons; and the percentage of conjugates where n is 1 is at least ninety percent.

86. The composition of claim 85 comprising conjugates of the formula

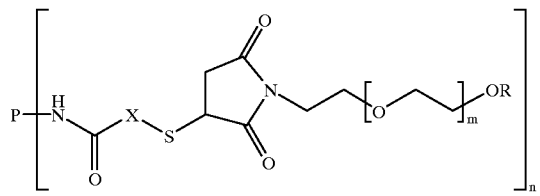

wherein n is an integer from 1 to 3; m is an integer from 450 to 900; R is lower alkyl; X is —(CH$_2$)$_k$— or —CH$_2$(O—CH$_2$—CH$_2$)$_k$—, and P is the residue of the erythropoietin glycoprotein without the amino group or groups which form an amide linkage with X.

87. The composition of according to claim 86 wherein the percentage of conjugates where n is 1 is at least ninety-two percent.

88. The composition of claim 86 wherein the percentage of conjugates where n is 1 is at least ninety-six percent.

89. The composition of claim 85 wherein the percentage of conjugates where n is 1 is from ninety percent to ninety-six percent.

* * * * *

UNITED STATES PATENT AND TRADEMARK OFFICE
CERTIFICATE OF CORRECTION

PATENT NO.    : 6,340,742 B1
DATED         : January 22, 2002
INVENTOR(S)   : Josef Burg, Bernd Hilger and Hans-Peter Josel It is certified that error appears in the above-identified patent and that said Letters Patent is hereby corrected as shown below:

Column 24,
Lines 42-54, delete

"
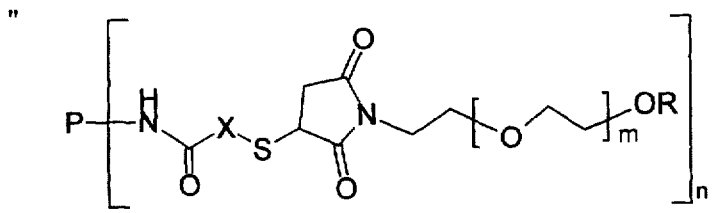

74. The conjugate of claim 67, of the formula:" and replace with the following:
-- 74. The conjugate of claim 67, of the formula:

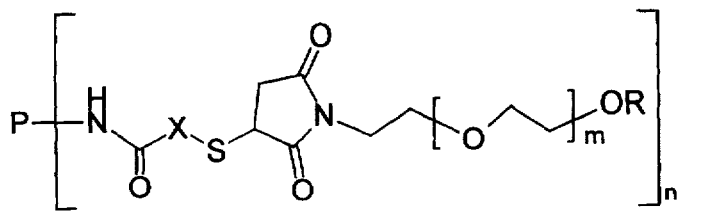

--

Signed and Sealed this

Twenty-third Day of April, 2002

Attest:

JAMES E. ROGAN
Attesting Officer     Director of the United States Patent and Trademark Office